US010881290B2

(12) United States Patent
Singer et al.

(10) Patent No.: US 10,881,290 B2
(45) Date of Patent: Jan. 5, 2021

(54) SYSTEM AND METHOD FOR OCULAR FUNCTION TESTS

(71) Applicant: BRAINSCOPE COMPANY, INC., Bethesda, MD (US)

(72) Inventors: Michael E. Singer, Bethesda, MD (US); Neil Samuel Rothman, Baltimore, MD (US); Gregory Mark Mahowald, Kensington, MD (US); David Anthony Lovejoy, Houston, TX (US)

(73) Assignee: BRAINSCOPE COMPANY, INC., Bethesda, MD (US)

( * ) Notice: Subject to any disclaimer, the term of this patent is extended or adjusted under 35 U.S.C. 154(b) by 42 days.

(21) Appl. No.: 16/420,510

(22) Filed: May 23, 2019

(65) Prior Publication Data

US 2019/0274540 A1 Sep. 12, 2019

Related U.S. Application Data

(63) Continuation of application No. 15/339,640, filed on Oct. 31, 2016, now Pat. No. 10,321,818.

(51) Int. Cl.
*A61B 3/032* (2006.01)
*A61B 5/16* (2006.01)
(Continued)

(52) U.S. Cl.
CPC .......... *A61B 3/032* (2013.01); *A61B 3/0025* (2013.01); *A61B 5/0013* (2013.01);
(Continued)

(58) Field of Classification Search
CPC ..... A61B 3/032; A61B 3/0025; A61B 5/0013; A61B 5/0075; A61B 5/16; A61B 5/4064; A61B 5/4076; A61B 5/486; A61B 5/6898
(Continued)

(56) References Cited

U.S. PATENT DOCUMENTS

| 5,422,689 | A | 6/1995 | Knapp et al. |
| 5,596,379 | A | 1/1997 | Kawesch |

(Continued)

FOREIGN PATENT DOCUMENTS

| DE | 102007028654 A1 | 1/2009 |
| GB | 2514529 | 12/2014 |

(Continued)

OTHER PUBLICATIONS

Cerebrovortex (Dec. 3, 2012) "Concussion effects within eye positioning reveals attention impaired deregulation of predictive visual tracking in the vertical component" [online]. Retrieved from: http://cerebrovortex.com (11 pages).

(Continued)

*Primary Examiner* — Collin X Beatty
(74) *Attorney, Agent, or Firm* — Finnegan, Henderson, Farabow, Garrett & Dunner, L.L.P.

(57) ABSTRACT

A system for use in performing ocular examinations, such as convergence and accommodation useful in diagnosing traumatic brain injury (including concussion), includes an assessment device. The assessment device includes a portable carrier having a visual target and a distance measurement component. The system may further include a communications channel and a companion device. The distance measurement component communicates via the communication channel with the companion device. The companion device stores one or more distances measured by the distance measurement component.

16 Claims, 10 Drawing Sheets

(51) Int. Cl.
*A61B 5/00* (2006.01)
*A61B 3/00* (2006.01)

(52) U.S. Cl.
CPC .............. *A61B 5/0075* (2013.01); *A61B 5/16* (2013.01); *A61B 5/4064* (2013.01); *A61B 5/4076* (2013.01); *A61B 5/486* (2013.01); *A61B 5/6898* (2013.01)

(58) Field of Classification Search
USPC ........................................................ 351/244
See application file for complete search history.

(56) References Cited

U.S. PATENT DOCUMENTS

| | | | |
|---|---|---|---|
| 5,668,622 | A | 9/1997 | Charbonnier et al. |
| 5,668,743 | A | 9/1997 | Kushelvesky |
| 6,042,231 | A | 3/2000 | Fateh |
| 6,592,223 | B1 | 7/2003 | Stern et al. |
| 6,739,722 | B2 | 5/2004 | Laguette et al. |
| 8,967,809 | B2 | 3/2015 | Kirschen et al. |
| 9,241,620 | B1 | 1/2016 | Kockan |
| 9,374,562 | B2 | 6/2016 | Trombley et al. |
| 9,928,399 | B2 * | 3/2018 | Chi .................... G06K 9/00087 |
| 9,958,939 | B2 * | 5/2018 | Ghajar ................. G06F 3/0482 |
| 2002/0099305 | A1 | 7/2002 | Fukushima et al. |
| 2004/0100620 | A1 | 5/2004 | Glaser |
| 2006/0087618 | A1 | 4/2006 | Smart et al. |
| 2013/0141697 | A1 | 6/2013 | Berry et al. |
| 2014/0085472 | A1 | 3/2014 | Lu et al. |
| 2014/0118685 | A1 | 5/2014 | Kawamura |
| 2015/0164315 | A1 | 6/2015 | Drobe |
| 2016/0029884 | A1 | 2/2016 | Kockan |
| 2016/0106315 | A1 | 4/2016 | Kempinski |
| 2016/0120402 | A1 | 5/2016 | Limon |
| 2016/0128568 | A1 * | 5/2016 | Bellamy .............. A61B 3/0083 351/209 |
| 2016/0192873 | A1 | 7/2016 | Kelly et al. |
| 2016/0205298 | A1 | 7/2016 | Zhou |
| 2016/0302661 | A1 | 10/2016 | Alberts et al. |
| 2016/0317019 | A1 | 11/2016 | Maddalena et al. |
| 2017/0000344 | A1 | 1/2017 | Visconti |
| 2017/0007167 | A1 | 1/2017 | Kostic et al. |
| 2017/0027805 | A1 | 2/2017 | Simmons |
| 2017/0039689 | A1 | 2/2017 | Solanki et al. |
| 2017/0202454 | A1 | 7/2017 | Steinmueller et al. |
| 2017/0209043 | A1 | 7/2017 | Gross et al. |
| 2017/0215723 | A1 | 8/2017 | Sakurada et al. |

FOREIGN PATENT DOCUMENTS

| | | |
|---|---|---|
| JP | 2007-097707 A | 4/2007 |
| WO | WO 2015/120438 A1 | 8/2015 |

OTHER PUBLICATIONS

Bernell Corporation (2016) Vergel™ Product Information [online]. Retrieved from: www.bernell.com/product/VERGEL/Screening-Tests (2 pages).

International Search Report and Written Opinion of the International Searching Authority dated Feb. 5, 2018, in corresponding PCT International Application No. PCT/US2017/059026.

* cited by examiner

SYSTEM AND METHOD FOR OCULAR FUNCTION TESTS

CROSS-REFERENCE TO RELATED PATENT APPLICATIONS

This application is a Continuation application of U.S. application Ser. No. 15/339,640, entitled "SYSTEM AND METHOD FOR OCULAR FUNCTION TESTS" and filed on Oct. 31, 2016, the contents of which are hereby incorporated by reference in their entirety.

TECHNICAL FIELD

The present disclosure relates generally to a system and method of assessing neurocognitive deficits, and more particularly to a system and method of testing ocular function.

BACKGROUND

Assessments of traumatic brain injury (TBI), including concussion, and other neurocognitive deficits may be assisted through ocular function testing. Concussion and other TBI can lead to changes in brain function, and variations in higher cortical brain functions such as vision may reveal underlying trauma. The visual system of the human involves roughly half of the brain's neurological circuits, and concussions and other TBIs frequently result in abnormalities in ocular functions, such as convergence (the turning inward of the eyes separately to focus on a near-field object), accommodation (the changing of the shape of the eye to alter lens shape for near-field and far-field focus), the vestibular-ocular reflex (VOR, the stabilization of focus during head movement), ocular muscle balance (alignment of the eyes), saccades (quick simultaneous movements of both eyes between two or more phases of fixation), and pursuit (the ability to follow a moving object). Ocular function testing during concussion assessment may include, for example the testing of eye tracking capability (e.g., smooth pursuit and saccade), and convergence and accommodation.

Further, the ocular function testing may include a strabismus test. Strabismus refers to a disorder in which the eyes do not look in exactly the same direction at the same time. For example, one eye may look straight ahead, while the other eye turns inward, outward, upward, or downward. Different methods may be used to test strabismus, including a light reflex testing and a cover testing.

Prior art ocular assessment techniques are either not suited for field deployment such as a sports sideline or a battlefield, or else are imprecise due to their manual nature. For example, large instruments, such as autorefractors and wavefront aberrometers, can measure refractive changes in the eye, but are not suited for field deployment. Imaging the surface of the eye using axial biometry or biomicroscopy is also not suited for use in non-specialized settings. Phoropter testing for accommodation requires a controlled environment and can take 15 minutes or longer. Similarly, eye-tracking manual testing techniques may include paper-and-pencil based forms, including for example vestibular-ocular motor screening (VOMS)), saccades test cards.

The above-mentioned conventional manual testing techniques suffer from many drawbacks. For example, manual near-point convergence and near-point accommodation tests are generally conducted by using a target for the subject to focus on, for example, a tongue depressor, which is moved towards and away from the subject. The subject identifies the point at which he or she notices a pre-identified visual event, such as the loss of focus of the target, a distortion in vision, the acquisition of focus, etc. Alternatively, for a near point of convergence test, a clinician may observe the subject's eyes and identify a loss of convergence, for example, as drifting of one eye. A complaint by clinicians is that these tests are subjective, inexact, and performed inconsistently. The distance measurements are prone to error because they require the person performing them (often but not always a physician) to hold the tongue depressor fixed in space while simultaneously trying to measure the distance to the subject. Measures such as the starting distance from the subject, the rate of movement of the target toward the subject, etc., can be difficult to control and measure in real time, resulting in inconsistencies and imprecision in performance and results. While imprecision is detrimental to accurate assessment of TBI including concussion, these drawbacks have the natural result of inhibiting adoption of these methods, depriving some routine assessments of a visual modality altogether.

The exemplary systems and methods disclosed herein are directed to addressing one or more of the problems set forth above during psychophysical ocular assessments and/or other deficiencies in the prior art.

SUMMARY

One aspect of the present disclosure is directed to a system for performing an ocular assessment on a subject. An exemplary system includes an assessment device that includes a portable carrier. The portable carrier can include a distance measurement component, and a visual target thereon viewable by a subject. The assessment device may further include a flashlight capable of shining light. In an illustrative embodiment, the system can further include a communications channel, and a companion device. The assessment device can communicate via the communications channel with the companion device. An exemplary companion device stores one or more distances measured by the distance measurement component. The distance measuring component can be configured to measure one or more distances between the assessment device and the subject.

Another aspect of the present disclosure is directed to a method of performing an ocular assessment on a subject. An exemplary method includes providing an assessment device. The assessment device can include a portable carrier that includes a distance measurement component, and a visual target thereon viewable by a subject. The assessment device may further include a flashlight capable of shining light. The method can further include providing a companion device. The companion device in an illustrative method communicates with the assessment device via a communications channel. An exemplary method can further include the steps of holding the assessment device at a distance from the subject, moving the assessment device, and recording one or more of distances from the assessment device to the subject during the moving of the assessment device. An illustrative method can further include transmitting one or more distances via the communications channel to the companion device, and in some embodiments, a set of distances can be stored in the companion device.

BRIEF DESCRIPTION OF THE DRAWINGS

The accompanying drawings, which are incorporated in and constitute part of this specification, and together with the description, illustrate and serve to explain the principles of various exemplary embodiments.

DETAILED DESCRIPTION

Figure 1:
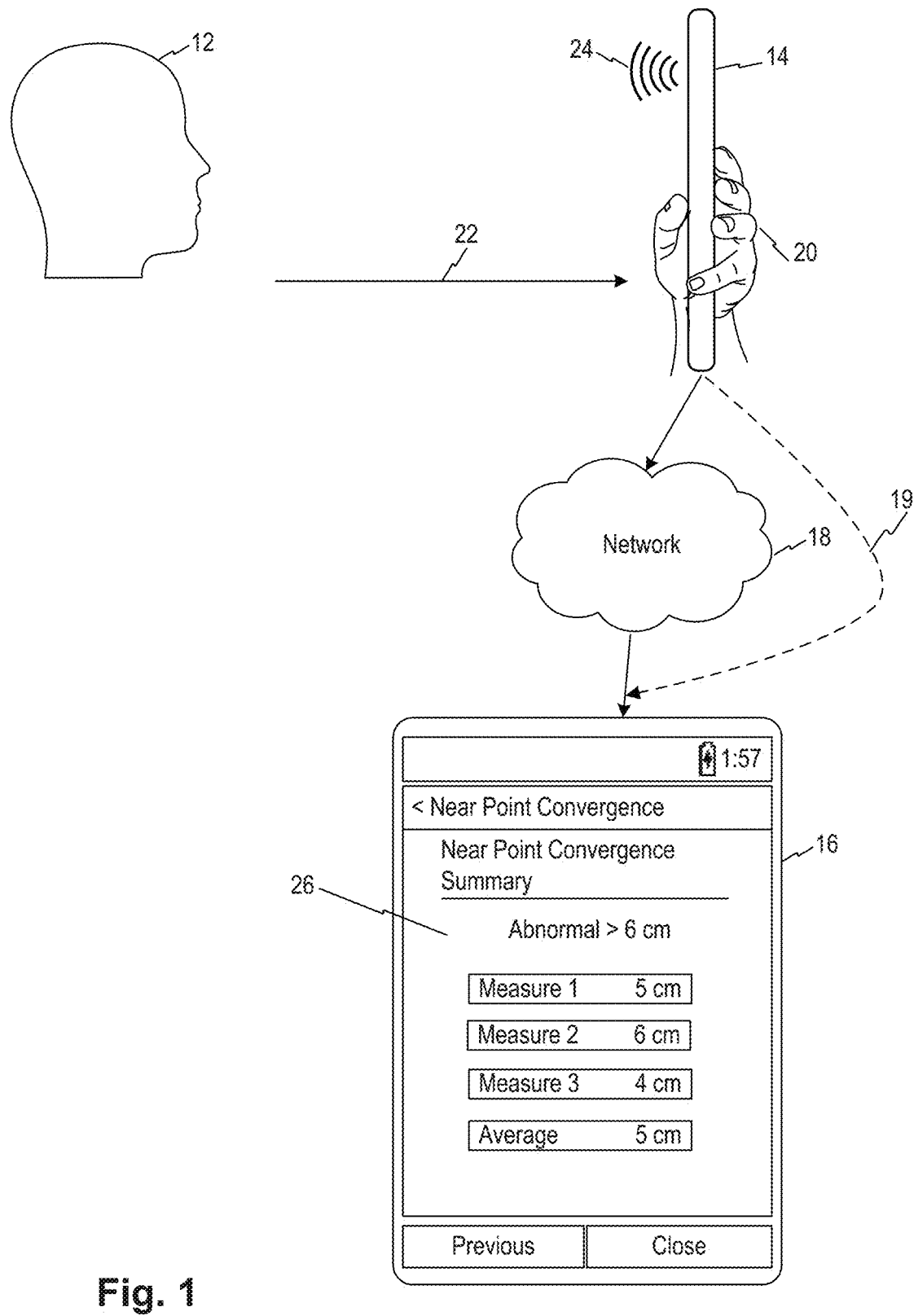
FIG. 1 is a schematic illustration of an exemplary system for testing ocular functions, according to an exemplary embodiment.

The disclosure is generally directed to a system for evaluating convergence and accommodation measures of ocular function. The system may include an assessment device. The assessment device includes a portable carrier including a distance measurement component that measures a distance from the assessment device to a subject, and a visual target thereon viewable by the subject. In an illustrative embodiment, the distance measurement may be performed automatically or semi-automatically or upon receipt of a trigger by a user, e.g., a button-push or release, a switch, altering the position or orientation of the device, a voice cue, etc. Further, in an exemplary embodiment, the rate of movement of the assessment device towards the subject may also be determined directly from the continuous data stream of distance measurement and be provided as a feedback to the user. Thus, simple near point convergence and near point accommodation tests may be automatically performed.

In an exemplary embodiment, the system may further include a communication channel and a companion device. The assessment device may communicate via the communication channel with the companion device. The companion device can store one or more distances measured by the distance measurement component, and the one or more distances can be measured by a trigger, such as pressing or pushing a button on the assessment device, either by a subject under test or a clinician conducting a test, where the test involves a subject looking at the visual target on the display. The companion device may further have a capability to analyze and calculate the one or more distances to generate a meaningful report for a clinician. Accordingly, the assessment device may wirelessly provide the distances to the companion device, seamlessly integrating the distance data in an information hub or a database that may operate on the companion device or operate in a remote "cloud" database.

Further illustrative embodiments of the present disclosure are directed to a method of testing convergence and accommodation of ocular function. The method may include providing an assessment device. The assessment device may include a portable carrier including a distance measurement component for measuring one or more distances from the assessment device to a subject, and a visual target thereon viewable by the subject. The assessment device may further include a timer for recording a time or a pace of the ocular assessment, or individual tests such as convergence and accommodation. In an exemplary embodiment, the assessment device can also further include an error message display for reporting an operation error to a user or for providing a feedback to the user. The feedback may include, but is not limited to, change of movement rate of the assessment device, off-target movement of the assessment device (e.g., left or right movement rather than straight movement toward the user), and misalignment of the assessment device (e.g., not aiming at a spot on the user's face). An illustrative embodiment of a method according to the present disclosure may further include providing a companion device. The exemplary companion device can communicate with the assessment device via a communications channel. In illustrative embodiments, the communications channel can be wired or wireless. e.g., a BLUETOOTH link or a WiFi link. The exemplary method can further include holding the assessment device at a distance from the subject, moving the assessment device, and recording a set of coordinates or distances from the assessment device to the subject during the moving of the assessment device. The method can further include transmitting the set of coordinates or distances via the communications channel to the companion device, the set of coordinates or distances are stored at least temporarily in the companion device. The present disclosure may provide the improvements associated with automation of the distance measurement for measuring the near point of convergence and accommodation to assist in the diagnosis of concussion and other forms of TBI and other neurocognitive deficits. Accordingly, the present disclosure enables the addition of ocular function testing which is a key clinical parameter for diagnosis of concussion and other forms of TBI and other neurocognitive deficits.

FIG. 1 is a schematic illustration of an exemplary system 10 for testing ocular functions, according to an exemplary embodiment of the present disclosure. As shown in FIG. 1, system 10 may include a subject 12 (e.g., a patient) who may be tested for ocular functions; an assessment device 14 having a target display and a distance measurement component; a network or communications channel 18, and a companion device 16 that communicates via network 18 with assessment device 14. The communications channel 18 is depicted in an illustrative embodiment as a wireless link, but it can also be, or include, a wired link as shown by dotted line 19 in FIG. 1. The communications channel can also include a networked information hub, such as that described in commonly assigned U.S. Provisional Patent Application No. 62/273,677 entitled "System and Methods for Networked Neurological Monitoring, Assisted Diagnosis and Data Collection and Management," which is incorporated by reference herein in its entirety.

Assessment device 14 is held by a hand 20 of a user at a distance (indicated by an arrow 22) from subject 12, located generally in front of subject 12. Assessment device 14 may be held by subject 12, for example, at an arm's length from subject 12. Alternatively, assessment device 14 may be held by another user, for example, a clinician who performs the ocular function test. Subject 12 can view a target displayed on the target display during testing, and as assessment device 14 is moved toward and away from subject 12, one or more distances from assessment device 14 to subject 12 may be automatically measured by the distance measurement component, which transmits and receives a signal 24 for distance measurement. A distance may be measured from the forehead of subject 12 or any other portion of subject 12.

Network 18 may include any type of network configured to facilitate communications and data exchange between assessment device 14 and companion device 16. Network 18 may include any type of direct physical link between assessment device 14 and companion device 16, such as USB cable. Network 18 may include a wireless link between assessment device 14 and companion device 16, for example, a BLUETOOTH. Wi-Fi link, or infrared optical link. Network 18 may further include a Local Area Network (LAN), a Wide Area Network (WAN), such as the Internet. Network 18 may be a single network or a combination of networks. Network 18 is not limited to the above examples and system 10 may implement any type of network that allows exchanging data and information between assessment device 14 and device 16, either directly or via an intermediary server or other information processing system.

Companion device 16 may be any type of computing device that is capable of exchanging data and information either directly with assessment device 14 or via network 18 with assessment device 14 and further of storing, analyzing, and displaying data and information. Example of such computing device may include, but not limited to, a point-of-care portable brain assessment device, such as the AHEAD family of products sold by BrainScope Company, Inc. of Bethesda, Md., a personal digital assistant (PDA), cellular telephone, desktop computer, laptop computer, server, and/or hand-held devices such as tablets or purpose-built instruments for collecting distance data from the assessment device 14. In exemplary system 10, device 16 may be a hand-held device running an application program and having a display 26 thereon for displaying information and data.

Figure 2A:
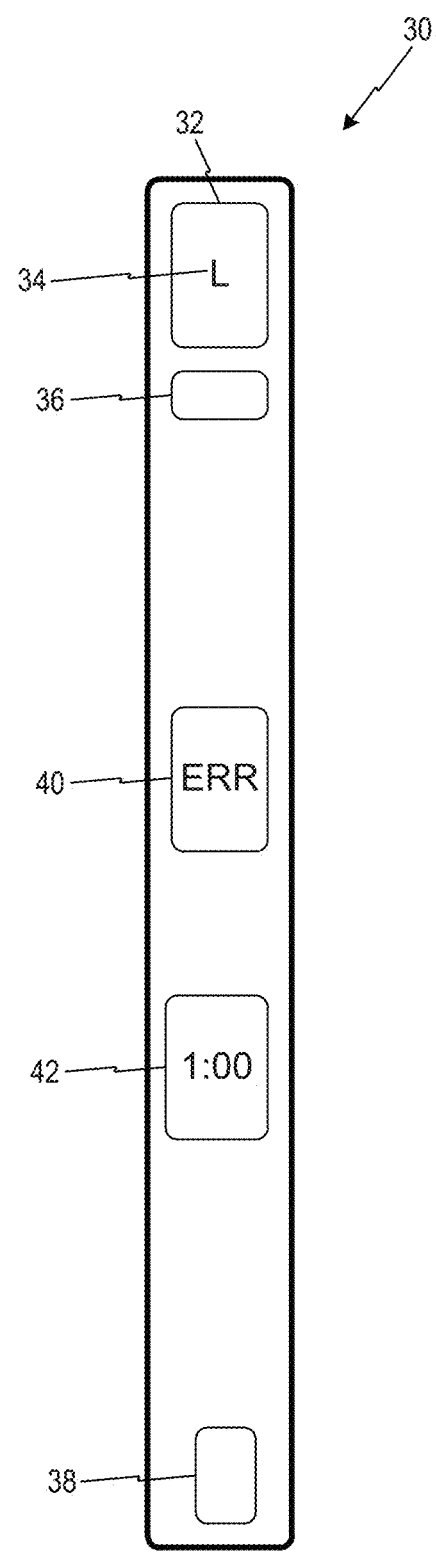
FIG. 2A is a schematic illustration of an exemplary assessment device that may be used with the exemplary system of FIG. 1, according to an exemplary embodiment.

FIG. 2A is a schematic illustration of an exemplary assessment device 30 that may be used with the exemplary system of FIG. 1, according to an exemplary embodiment. In an illustrative embodiment, assessment device 30 can be configured to include a portable carrier that includes a first display 32 thereon for displaying a visual target 34 viewable by a subject. Display 32 can be of any suitable format or size, and can be electronic or formed as indicia on the carrier. Further, an illustrative embodiment can include a distance measurement component 36 that measures a distance from assessment device 30 to a subject. A second display 40 can be included thereon for displaying, for example, instructions, error messages concerning the operation of the assessment device 30, feedback information to the user, etc. In an illustrative embodiment a timer 42 can be included, having a display for displaying a time of an ocular function test, for example. The locations and layout of first display 42, second display 40, and timer 42 on assessment device 30 may be configured based on different testing environments (e.g., sports sideline or clinician's office). For example, timer 42 and second display 40 may be configured to locate on an opposite side of the device from first display 32 to avoid distraction of the subject/patient.

In an illustrative embodiment, assessment device 30 may further include a trigger mechanism for indicating an event to be recorded. An exemplary trigger is button 38 that, for example, can be pressed or pushed by the subject or another user, such as a clinician who conducts the ocular function test. The time, distance, any error message, any feedback, and/or other information or measurement results may be transmitted in a real-time communication to companion device 16 of FIG. 1 for analysis, display, and storage. Alternatively, assessment device 30 may download the time, distance, any error message, any feedback and/or other information or measurement results later to companion device 16 versus the real-time communication to companion device 16.

In some embodiments, a companion device is not available or assessment device 30 may be employed to function completely without the companion device. The time, distance, any error message, any feedback, and/or other information or measurement results may be processed locally on assessment device 30. That is, assessment device 30 is configured to have a capacity for analysis, display, and storage of the time, distance, any error message, any feedback, and/or other information or measurement results.

In some embodiments, assessment device 30 may further include a micro-controller, an alphanumeric display, a BLUETOOTH RF (radio frequency) transceiver, a power/battery management module and a flashlight capable of shining light.

In some embodiments, distance measurement component 36 may include a sensor that enables assessment device 30 to measure a distance from assessment device 30 to a subject, for example the subject's face, when button 38 is pressed by the user or a clinician in response to specific observations as part of each test. Distances can also be continuously measured. The measured distance data may be wirelessly transmitted to a handheld device, for example, device 16 in FIG. 1.

In some embodiments, distance measurement component 36 may be configured to include the use of IR (infrared) or optical means to perform the distance measurement. In some embodiments, distance measurement component 36 may be configured to include an array of infrared sensor transmitter/receiver pairs to improve distance measurements (e.g., accuracy). A single infrared sensor transmitter/receiver pair may have a narrow optical field of view that typically ranges from about 10 degrees to about 15 degrees. This requires an accurate positioning and alignment of device 30 and reduces measurement accuracy at longer distances. Utilizing an array of infrared sensor transmitter/receiver pairs may effectively increase the optical field of view by, for example 2 fold from a range of about 10 degrees to about 15 degrees to a range of about 20 degrees to about 30 degrees, respectively. The array of infrared sensor transmitter/receiver pairs may be mechanically spaced to enable an overlap in the optical field of view. Accordingly, the sensitivity of alignment of assessment device 30 may be minimized and the distance measurement accuracy at longer distances may be improved.

Additionally, the array of infrared sensor transmitter/receiver pairs may provide a measurement of azimuth and elevation of assessment device 30 and a positional feedback. Further, the positional feedback may be incorporated into a display (e.g., second display 40 in FIG. 2A) of assessment device 30 to provide a visual indicator. The visual indicator may include a signal strength indicator that changes color as assessment device 30 becomes optimally positioned, or a Bullseye type of target that displays and moves towards the center as assessment device becomes optimally positioned. Further, the positional feedback may be used to generate an audible tone to guide the user in optimizing the position and alignment of assessment device 30 relative to a target. Thus, in some embodiments, by employing an array of infrared sensor transmitter/receiver pairs, distance measurement inaccuracies may be addressed. Further, a user may be assisted in positioning and/or aiming assessment device 30 to minimize the sensitivity associated with positioning assessment device 30 correctly.

In some embodiments, distance measurement component 36 may be configured to include one or more camera-based sensor to automate the distance measurement. The measurement of distance can be based on image processing producing pixel number variation of images from a digital camera imaging a designated target of a known shape. The designated target could be of any shape located on the patient, for example on a BrainScope AHEAD electrode headset or other simple adhesive backed material placed on the subject.

In some embodiments, distance measurement component 36 may be configured to include one or more ultrasonic-based sensor to automate the distance measurement. An ultrasonic sensor generates high-frequency sound waves that travel towards a subject (e.g., subject 12 of FIG. 1). The echoing sound waves from the subject can be received by the sensor and evaluated. The measurement of distance from the subject to device 30 (e.g., target 34 displayed on first display 32) can be determined by measuring the time interval between sending the sound wave signal and receiving the echo sound wave signal.

In some embodiments, a distance measurement component itself may be a separate device, or part of a separate device, from assessment device 30 (which may or may not have a built-in distance measurement component). Such a separate device can be worn by a subject (e.g., subject 12), for example, on the head. In an exemplary embodiment, the separate device can take the form of an electrode array headset, a data acquisition module such as that employed in the AHEAD family of products sold by BrainScope Company, Inc. of Bethesda, Md., etc. In other embodiment, where the separate device is worn in a plane outside that of the eyes, a correction factor can be added or subtracted to measured distance to account for this offset. The separate distance measurement device can determine a distance between assessment device 30 and subject 12, in an illustrative embodiment, by measuring a distance from subject 12 to target 34 that may employ one of the aforementioned techniques including IR, ultra sound wave, and camera-based sensor. Additionally, the measurement of distance from subject 12 to target 34 may be conducted by image-processing the observed size of target 34 compared to its known dimensions (i.e., the farther away, the smaller the target appears), or the observed brightness of a target compared to its actual brightness (i.e., the farther away, the dimmer the object appears). Still further, the measurement of distance from subject 12 to target 34 may be conducted by using a time-of-flight camera and/or photonic-mixer-device, which emit a light pulse that is reflected and the distance is measured by determining the turn-around time the pulse needs to travel from the sender.

In some embodiments, device 30 with a built-in distance measurement component may be worn, for example on the head of subject 12 instead of being held in front of subject 12 at a certain distance. An object with a viewable target thereon may be used to automatically determine a distance from device 30 (i.e., subject 12) to the object via the viewable target on the object by the built-in distance measurement component. The object is positioned and held in front of subject 12 at a certain distance from subject 12, and is moved towards device 30 (i.e., subject 12). The object may be a second device 30, or a simple object like a tongue depressor with indicia forming a viewable target, a display, etc. as described above. In some embodiments, device 30 may further include an audio component to prompt for the measured distance, indicate an operation error of device 30, play instructions or provide a feedback to subject 12 or the user.

Figure 2B:
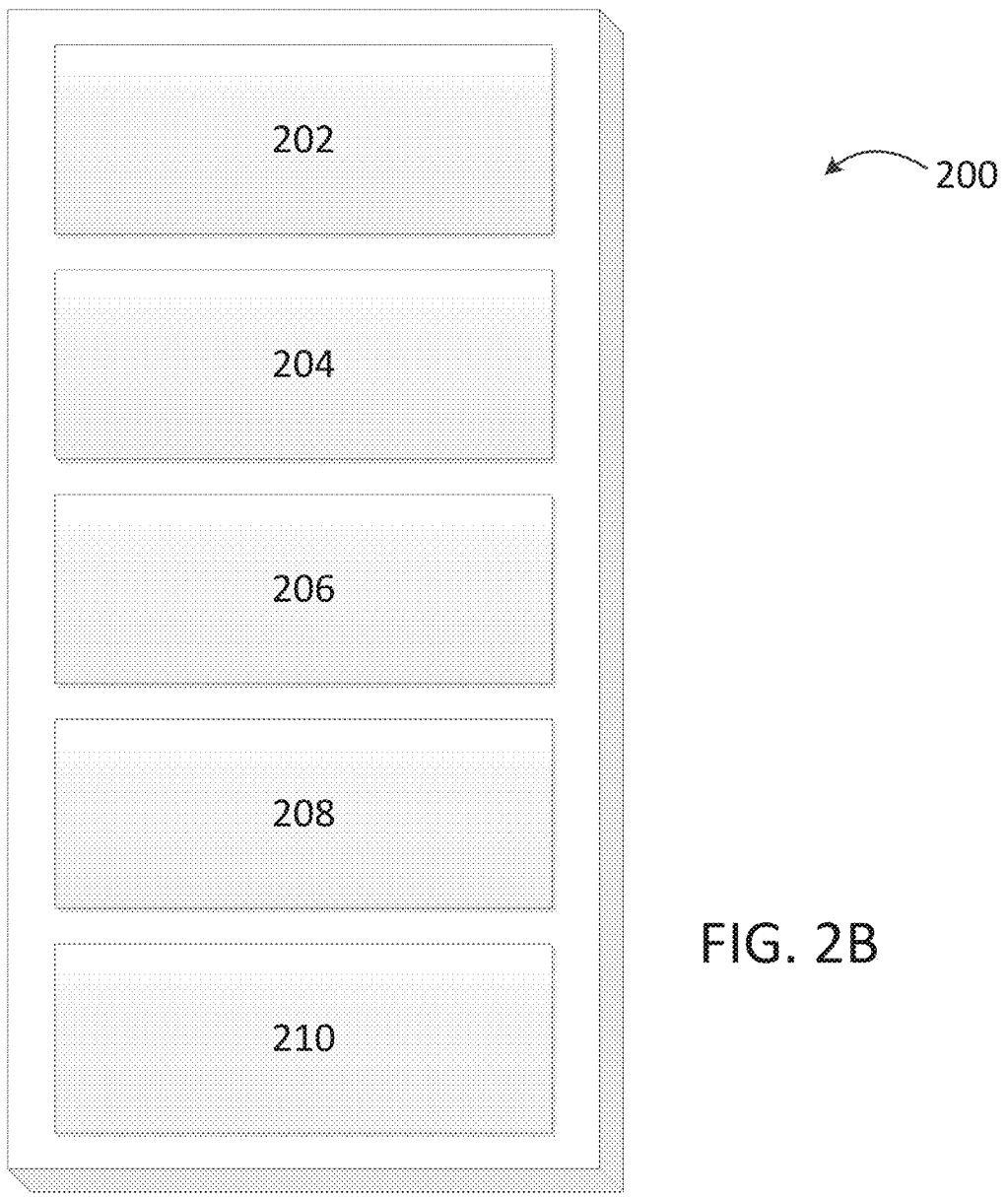
FIG. 2B is a schematic illustration of an exemplary assessment device that may be used with the exemplary system of FIG. 1, according to an exemplary embodiment.

FIG. 2B shows an additional schematic view of assessment device 200, according to an exemplary embodiment. Assessment device 200 may include a distance measuring component 202, a microcontroller 204, a power source 206, and an antenna (e.g., for near field communication (NFC) or a transceiver 208 (e.g., for BLUETOOTH. BLUETOOTH low energy (BLE), etc., communication), and one or more Input/output device 210. Distance measuring component 202 can be configured to send and receive infrared signals, for example. Microcontroller 204 can be programmed with instructions to control the overall operation of assessment device 200. Transceiver 208 can be configured to wirelessly communicate with a companion device, as described herein, using one or more wireless communication methods. The one or more wireless communication methods may include, for example, radio data transmission, BLUETOOTH, BLE, near field communication (NFC), Wi-Fi, infrared data transmission, electromagnetic induction transmission, and/or other suitable electromagnetic, acoustic, or optical transmission methods. Power source 206 may be configured to power distance measuring component 202, microcontroller 204, transceiver 208, and input/output device(s) 210, and any other electronic components of assessment device 200. Assessment device 200 may further include a flashlight capable of shining light that may be powered by power source 206.

Figure 3:
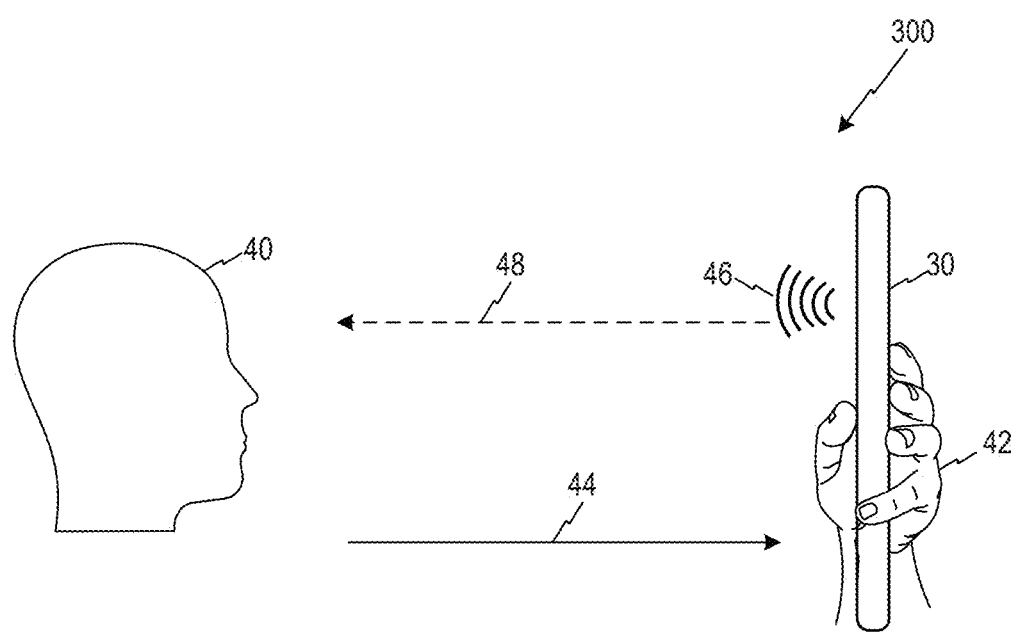
FIG. 3 is an exemplary diagram for convergence or accommodation test that may use the exemplary assessment device in FIG. 2A, according to an exemplary embodiment.

FIG. 3 is an exemplary diagram 300 for convergence or accommodation test that may use exemplary assessment device 30 in FIG. 2A, according to an exemplary embodiment. As shown in FIG. 3, a subject 40 may stand up or sit for a convergence or accommodation test of ocular function. Assessment device 30 is positioned and held, for example by a hand 42, at a certain distance (indicated by arrow 44) in front of subject 40 either by subject 40 extending an arm length, or by another user such as a clinician. The distance measurement component of assessment device 30 sends and receives a signal 46 to continually measure a plurality of distances from assessment device 30 to subject 40 while assessment device 30 is kept moving towards subject 40. Detailed discussions of convergence and accommodation tests will be described below in FIGS. 4 and 6, respectively.

Convergence test is to measure the eye ability to view a near target without double vision (also refers to as a near point convergence test (NPC)). A subject is seated and may wear corrective lenses (if needed) during the test. An examiner (e.g., a clinician) is positioned at a distance in front of the subject and observes eye movement of the subject during this test. The subject focuses on a small target (e.g., approximately 14 point font size) at an arm's length from the subject and slowly brings the target toward the subject, for example the tip of the subject's nose. The subject is instructed to indicate when the subject sees two distinct images of the target or when the examiner observes an outward deviation of one eye. For the convergence test, blurring of the image of the target may be ignored. The distance between the target and the tip of nose is measured and recorded. This test may be repeated a plurality of times, such as a total of 3 times with measured distances recorded each time. It may be considered abnormal if the distance of near point of convergence is equal to or greater than about 5 cm from the nose tip of the subject.

Figure 4:
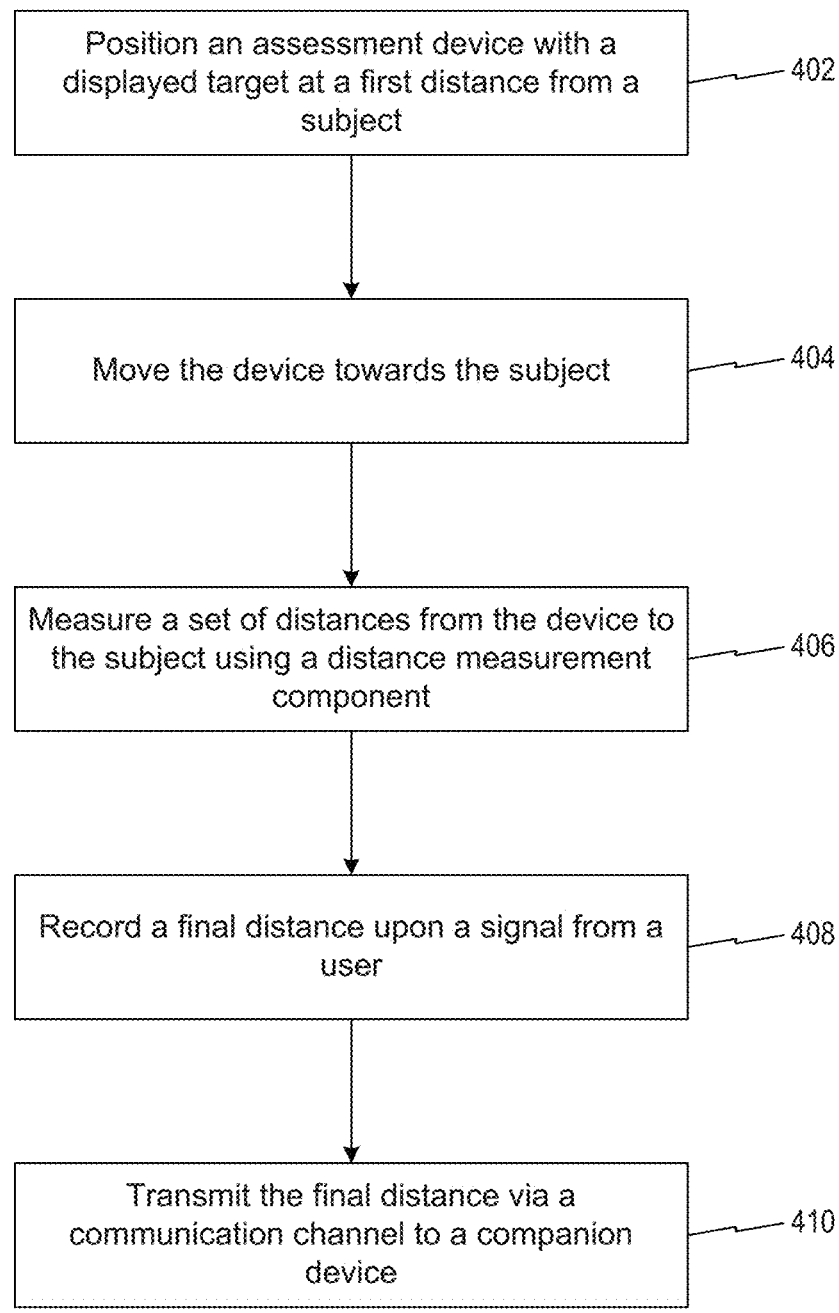
FIG. 4 is a flow chart of a process for testing convergence that may use the exemplary diagram of FIG. 3, according to an exemplary embodiments.

FIG. 4 is a flow chart of a process 400 for testing convergence (i.e., near point convergence) that may use the exemplary diagram of FIG. 3, according to an exemplary embodiment. In step 402, assessment device 30 is placed at a certain distance from a subject 40 who is under evaluation. The subject visually focuses on a small target displayed on first display 32 of assessment device 30, for example a character "L" 34 of about 14-point font size, as displayed on first display 32. In step 404, assessment device 30 is kept moving continuously towards subject 40, by either the subject, or another user such as a clinician. The moving of assessment device 30 may be slow, such as at a pace of 1 cm per second. In step 406, a set of distance from assessment device 30 to subject 40 are measured and recorded automatically by assessment device 30, specifically by a distance measurement component such as an array of infrared transmitters and receiver pairs that transmit and receive signals 46. The set of recorded distances may be further transmitted to a device, for example, companion device 16 for analysis, display and/or storage. In step 408, a final distance is measured and recorded by the distance measurement component. The final distance is calculated at the time of a button (button 38 on assessment device 30) being pressed by subject 40 when a singular vision of the small target is no longer maintained to subject 40. Alternatively, the final distance is calculated at the time of a trigger. In this example and in other examples disclosed herein, a trigger can take a variety of forms, such as pressing or releasing button 38 or another switch on assessment device 30, changing the orientation or position of the assessment device using an internal accelerometer, GPS sensor, gyroscope, magnetometer, photometer, or proximity sensor, or the detection of a command or key-word by a microphone and associated voice-recognition software, located either on the device or remotely, such as on device 16, or from a separate component such as a headset worn, for example, by the subject or another user. The trigger condition can be signaled by, for example, the clinician when an evaluation event occurs, for example the clinician observes an outward deviation of one eye of subject 40. The final distance may be the distance from assessment device 30 (e.g., where signal 46 is transmitted and/or received) to the nose tip of subject 40. Alternatively, the final distance may be the distance from assessment device 30 (e.g., where signal 46 is transmitted and/or received) to the forehead of subject 40. In step 410, the final distance is transmitted via a communications channel to a companion device, for example, companion device 16 via network 18 for analysis, display and/or storage. The above steps may be repeated as many times as necessary, for example 3 times to obtain an average final distance.

Figure 5:
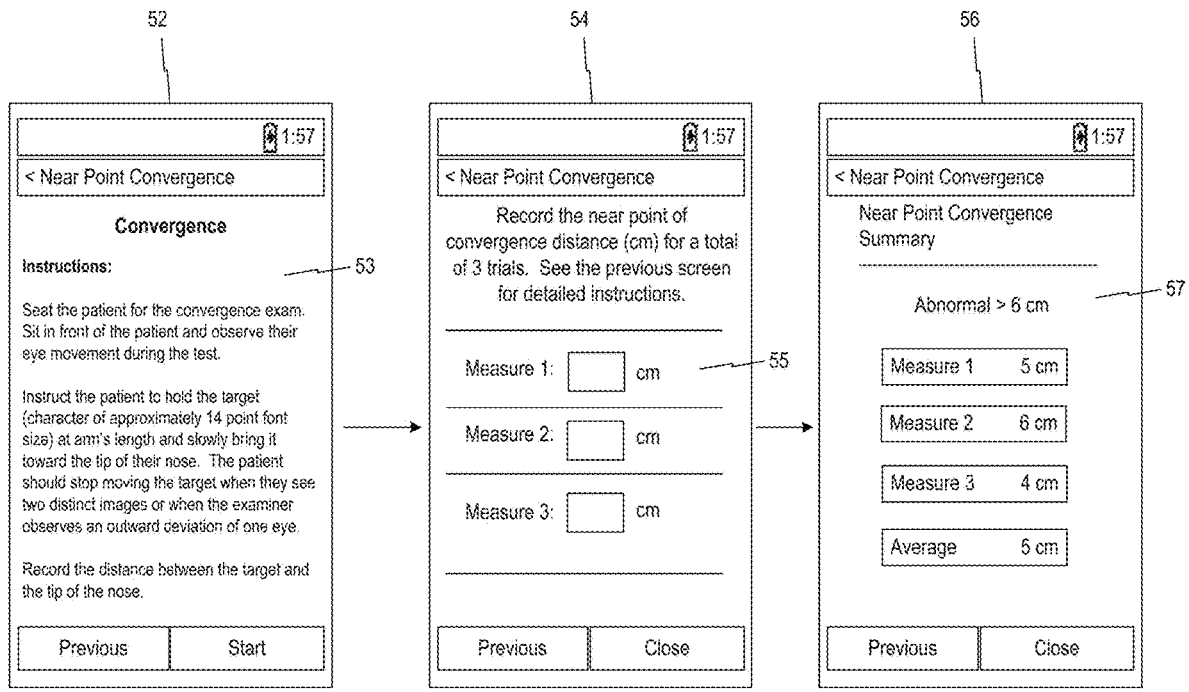
FIG. 5 is a schematic illustration of screenshots of a companion device that may be used for convergence test conducted in FIG. 4, according to an exemplary embodiment.

FIG. 5 is a schematic illustration of exemplary screenshots of a companion device that can be used for convergence test conducted in FIG. 4, according to an exemplary embodiment. In this exemplary embodiment, the companion device is device 16 in FIG. 1. Screenshot 52 primarily displays instructions 53 of convergence test. Instructions 53 may be provided to subject 40 prior to testing, for example being read to subject 40 by the clinician or being read by subject 40, such that subject 40 knows what to do and what to expect during the testing. Screenshot 54 primarily displays final distance recordings 55 of convergence test. In this example, the final distance is measured 3 times as indicated by measure 1, measure 2 and measure 3, respectively. The values of measures 1 to 3 may be entered automatically from assessment device 30 via network 18. Alternatively, the values of measures 1 to 3 may be entered manually by the clinician. NPC test summary is displayed, as shown on screenshot 56. Summary 57 displays 3 final distances, and an average final distance calculated based on the 3 final distances. Also shown on screenshot 56 is a criteria of NPC test, for example, if the average final distance is greater than 6 cm, then NPC is considered as abnormal In some embodiments, accommodation testing may be performed using the exemplary diagram of FIG. 3. In the example embodiment, the accommodation test is referred to as accommodation "Push Up" test (also referred to as near point accommodation (NPA) test), which measures the ability of the eye to adjust its lens to keep objects in focus. For this test, a small object, for example a letter of 4 point font, is used as a target to better control accommodation. Corrective lenses may be worn if needed. A subject is instructed to close one eye and slowly move the target towards the subject, such as the nose tip of the subject until the target becomes blurry. A distance is measured from the target to the subject when the target (i.e., the letters) becomes blurry. Each eye may be tested separately. In some embodiments, it is considered as abnormal when an accommodation distance is greater than 15 cm, for example from the nose tip of the subject.

Figure 6:
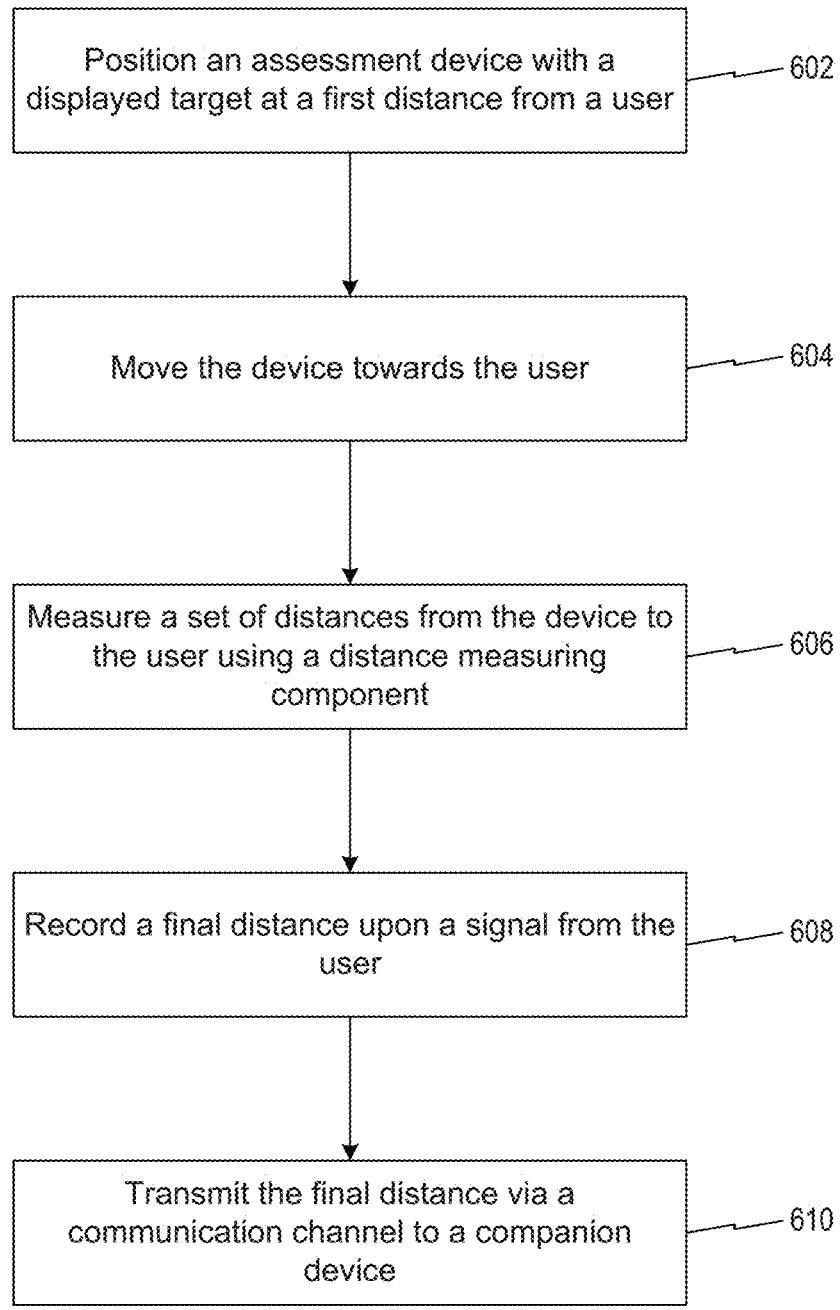
FIG. 6 is a flow chart of a process for testing accommodation that may use the exemplary diagram of FIG. 3, according to an exemplary embodiments.

FIG. 6 is a flow chart of a process 600 for testing accommodation (NPA) that may use the exemplary diagram of FIG. 3, according to an exemplary embodiment. In step 602, assessment device 30 is placed at a certain distance from a subject 40 who is under test. The subject focuses eyes on a small target displayed on first display 32 of assessment device 30, for example a character "L" 34 of about 4-point font size, as displayed on first display 32. In step 604, assessment device 30 is moved in relation to subject 40, which may be performed by either the subject or another user, such as a clinician. The moving of assessment device 30 may be slow, such as at a pace of 1 cm per second. In step 606, a set of distance from assessment device 30 to subject 40 are measured and recorded automatically by assessment device 30, specifically by a distance measurement component such as an array of infrared transmitters and receiver pairs that transmit and receive signals 46. The set of recorded distances may be further transmitted to a device, for example, companion device 16 for analysis, display and/or storage. In step 608, a final distance is measured and recorded by the distance measurement component. The final distance is calculated at the time of a button (button 38 on assessment device 30) being pressed by the user, or another trigger condition is created, when the small target is blurry to subject 40. Alternatively, the final distance is calculated at the time of the trigger condition (e.g., a button pressed by the clinician when subject 40 indicates to the clinician that the small target is blurry). The final distance may be the distance from assessment device 30 (e.g., where signal 46 is transmitted and/or received) to the nose tip of subject 40. Alternatively, the final distance may be the distance from assessment device 30 (e.g., where signal 46 is transmitted and/or received) to the forehead of subject 40. In step 610, the final distance is transmitted via a communication channel to a device, for example, companion device 16 via network 18 for analysis, display and/or storage. The above steps may be performed for each eye of subject 40, separately. In some embodiments, the above steps may be repeated as many times as necessary for each eye, respectively, for example 3 times to obtain an average final distance.

Figure 7:
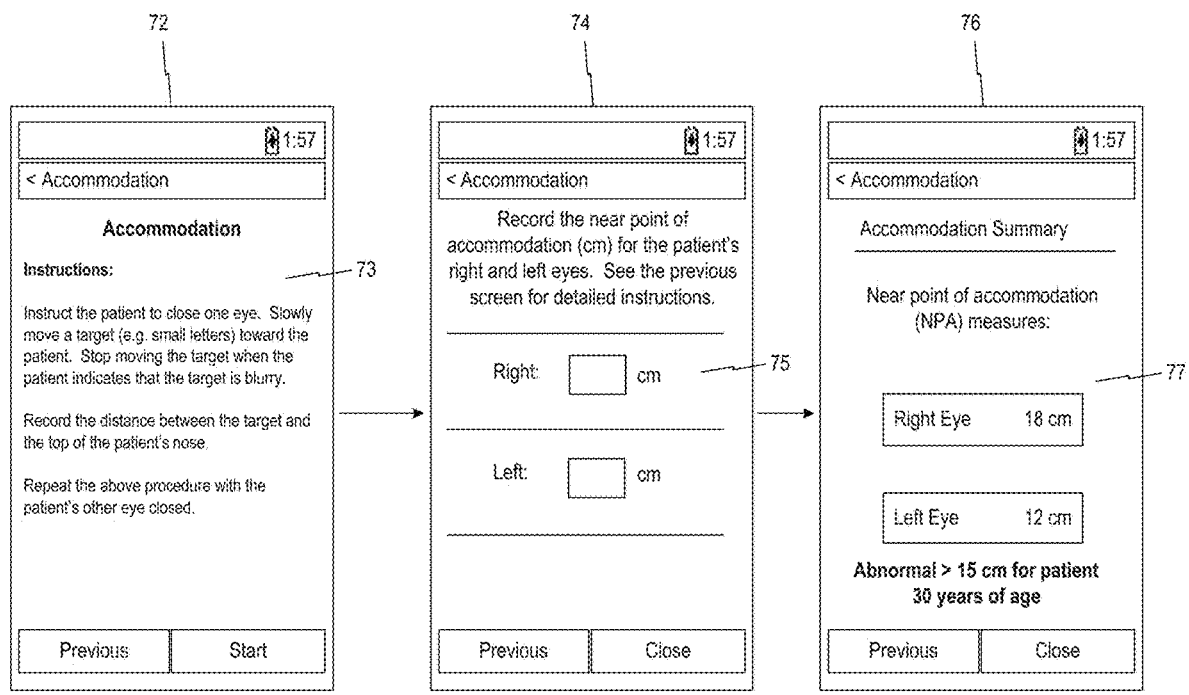
FIG. 7 is a schematic illustration of screenshots of a companion device that may be used for accommodation test conducted in FIG. 6, according to an exemplary embodiment.

FIG. 7 is a schematic illustration of screenshots of a companion device that may be used for accommodation test conducted in FIG. 6, according to an exemplary embodiment. In this exemplary embodiment, the companion device is device 16 in FIG. 1. Screenshot 72 includes displaying instructions 73 of accommodation test. Instructions 73 may be provided to subject 40 prior to testing, for example being read to subject 40 by the clinician or being read by subject 40, such that subject 40 knows what to do and what to expect during the testing. Screenshot 74 includes displaying final distance recordings 75 of accommodation test for each eye (i.e., right eye and left eye). In this example, the final distance on screenshot 74 may be an average distance obtained from a plurality of measures for each eye, respectively. Alternatively, the final distance on screenshot 74 may be a one-time distance obtained from a single measurement for each eye, respectively. The values of the final distances may be entered automatically from assessment device 30 via network 18. Alternatively, the values of the final distances may be entered manually by the clinician. NPA test summary is displayed, as shown on screenshot 76. Summary 77 includes the recorded final distances for right eye and left eye, respectively. Also shown on screenshot 76 is a criterion of an NPA test, for example, if the final distance is greater than 15 cm for a subject older than 30 years old, then NPA is considered as abnormal.

In some embodiments, a final distance from the assessment device to the patient may only be measured once the near point (e.g., for NPC test) is reached and the user (either the subject or another user, such as a clinician) creates a trigger condition, without measuring and recording a set of distance data prior to the final distance. In some embodiments, continuous distance measurement may be performed to record a plurality of distance data continuously throughout the test prior to recording a final distance. The present disclosure may improve distance measurement accuracy (e.g., for NPC and NPA tests) by employing a combination of outlier rejection and predictive algorithms. Such improvements may be enabled through the use of continuous distance measurement as the assessment device (e.g., assessment device 30) is being moved toward the subject during the convergence or accommodation test.

In some embodiments, a final distance measurement at the time of a trigger may be identified as an outlier (e. g., greater than 3 standard deviations away from the expected distance value) based on all distance data points recorded up to that final distance point in time. For example, if the assessment device is inadvertently moved slightly away from the subject when the button is pressed, the final distance recorded may be much greater than the correct final distance to the subject. Having a series of distance data points up to that final point in time may allow the use of extrapolation or a predictive algorithm to determine a likely distance measurement which can be compared to the actual measurement.

Figure 8:
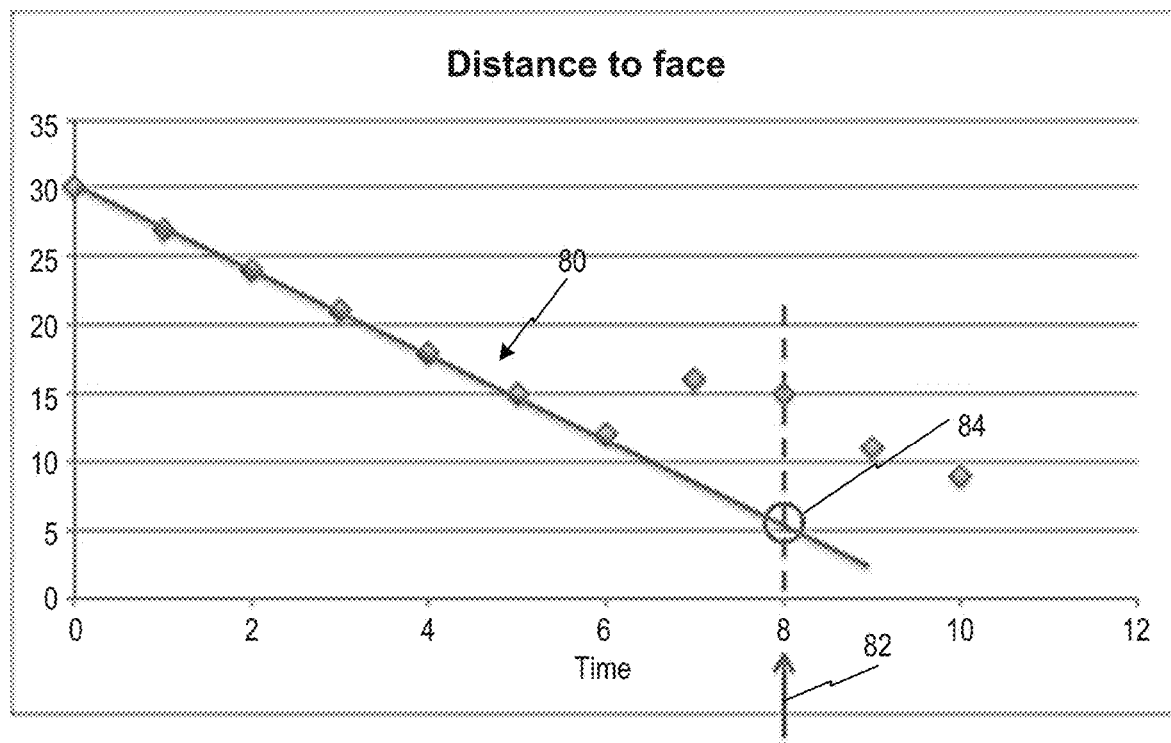
FIG. 8 is an exemplary plot of distance data acquired during convergence or accommodation test according to the exemplary diagram in FIG. 3.

FIG. 8 is an exemplary plot 80 of distance data for outlier detection that may be acquired during convergence or accommodation test according to the exemplary diagram in FIG. 3. As shown in FIG. 8, a set of distance data points in time are recorded while the assessment device is being moved towards the subject (e.g., the subject face). Just before the button of the assessment device is pressed at 8 seconds indicated by arrow 82, the assessment device is moved and there is an evident shift in the data. Extrapolation or a predictive algorithm may identify the "correct" distance, as shown by the open circle 84. For illustrative purpose only, the plot shows an exaggeration of what would likely actually happen in practice, but even minor deviations may be detected in this way. If there is a significant shift in the data, the assessment device may reject the distance measurement and the user would be informed that the test needs to be repeated.

In some embodiments, a feedback may be provided to a user that the assessment device is moving "off target" or in an irregular fashion. Since having the assessment device pointed directly at the subject's face is helpful in determining an accurate distance measurement, providing a feedback to the user may increase the accuracy of measurements obtained by the assessment device. If operated correctly, the distance to the subject's face should be decreasing in a fairly consistent manner until the near point of convergence or accommodation is reached. However, this can't be detected unless a targeting method is employed (e.g., aiming at a spot on the subject's face) or there is some other type of feedback. By measuring the distance to the subject's face continuously, misalignment may be detected since there will be variation in the rate of change of distance or the distance may actually increase rather than decrease. This can then be used to provide a feedback to the user to realign the assessment device.

Figure 9:
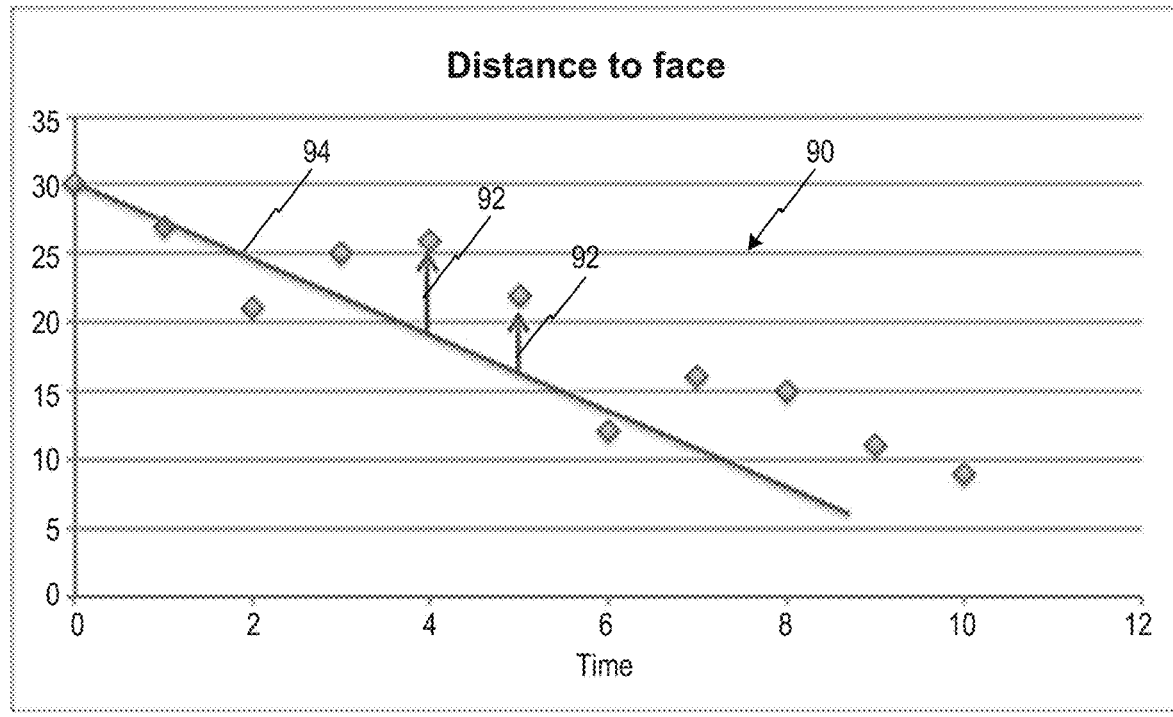
FIG. 9 is another exemplary plot of distance data acquired during convergence or accommodation test according to the exemplary diagram in FIG. 3.

FIG. 9 is another exemplary plot 90 of distance data for user feedback and device alignment that may be acquired during convergence or accommodation test according to the exemplary diagram in FIG. 3. As shown in FIG. 9, a set of distance data points are acquired while the assessment device is being moved toward the subject's face. In this case the deviations (shown as arrows 92) from the expected path (shown as a straight line 94) indicate that the user needs to realign the assessment device with the subject's face. The specific criteria for determining the expected path and what the acceptable deviation may vary based on tests. In some embodiments, the rate of assessment device movement may also be determined directly from the continuous data stream and be provided as a feedback to the user.

In some embodiments, smooth pursuits test may be performed using exemplary system 10 of FIG. 1. Smooth pursuits test is to test the ability of eyes to follow a slowly moving target. A subject and an examiner are seated. The examiner may hold assessment device 14 of FIG. 1 at a distance of, for example 3 feet, from the subject. The subject is instructed to maintain focus on a target (e.g., a target displayed on assessment device 14) as the examiner moves the target smoothly in a horizontal direction 1.5 feet to the right and 1.5 feet to the left of midline. One repetition is complete when the target moves back and forth to the starting position. One or more repetitions may be performed. In an exemplary test, the target may be moved at a rate requiring about 2 seconds to fully translate from left to right and about 2 seconds to fully translate from right to left. The test may be repeated with the examiner moving the target smoothly and slowly in a vertical direction 1.5 feet, above and 1.5 feet, below midline for 2 complete repetitions up and down. Again, the target may be moved at a rate requiring about 2 seconds to move fully upward and 2 seconds to move fully downward.

In some embodiments, an eye saccades test may be performed using exemplary system 10 of FIG. 1. Saccades tests evaluate the ability of the eyes to move quickly between targets. A subject and an examiner are seated. For horizontal saccades test, the examiner may holds two single points horizontally (e.g., two separate targets displayed on two assessment devices 14, respectively.) at a distance of about 3 feet from the subject, and 1.5 feet to the right and 1.5 feet to the left of midline such that the subject may gaze about 30 degrees to left and about 30 degrees to the right. The subject is instructed to move their eyes as quickly as possible from point to point. One repetition is complete when the eyes move back and forth to the starting position, and one or more repetitions may be performed.

In some embodiments, a number-naming or character-naming test may be performed using exemplary system 10 of FIG. 1. Such a test in exemplary embodiments evaluates the tracking ability of the eyes. For example, a test can be based on measurement of the speed of rapid number-naming or character-naming by having a subject read aloud a series of single-digit numbers or characters while scanning test cards or other indicia-bearing carrier or surface, which can be hard-copy or any other type of display. Standardized instructions can be used, which can include a prescribed time period. The exemplary test can include, for example, one practice (demonstration) card and 3 test cards. To perform the exemplary test, participants can be asked to read characters from left to right as quickly as possible but without making any errors. The time to complete the test and the number of errors can be recorded. A subject may read a row of numbers or characters displayed on an assessment device, for example assessment device 30 of FIG. 2A. Timer 42 of assessment device 30 may be used to record a time for scoring, and acts as a start/stop for stopwatch. Second display 40 of assessment device 30 may be used to denote an error message (e.g., how many numbers are read incorrectly) during the reading. Such time and error messages may be streamed to device 16 running a software application thereon that supports an exemplary test routine, such as a reading or scanning test, for analysis, display and/or storage.

In some embodiments, strabismus test may be performed using exemplary system 10 of FIG. 1. Strabismus test is to evaluate the size of the eye misalignment. In one exemplary embodiment, a light reflex testing may be conducted by using the flashlight of assessment device 30. A patient is instructed to look at a point of light shed from the flashlight of assessment device 30 that is held about three feet from the patient's face. The light reflexes are evaluated to determine whether they are located in the same spot in each pupil of eye. If the light reflexes are symmetric, then the eyes are identified as in alignment without strabismus. If the light reflexes fall asymmetrically in the pupils of eyes, then the eyes are identified as misaligned with strabismus. Such light reflexes can estimate the size of the strabismus by determining how far the deviated light reflex is off-center of the eye pupil. In another exemplary embodiment, a covering testing for evaluating strabismus may be conducted by using visual target 34 of first display 32. A patient is instructed to look at and fixate on visual target 34 held at about three feet from the patient's face while covering one eye. The uncovered eye is evaluated. A clinician observes the uncovered eye to determine whether strabismus is present to the uncovered eye. If the uncovered eye does not shift position, then the uncovered eye is identified as aligned without strabismus. If the uncovered eye changes position as the uncovered eye shifts to look at visual target 34, then the uncovered eye is identified as misaligned with strabismus.

In some embodiments, other ocular functions that are not discussed in the present disclosure may be performed using exemplary system 10 of FIG. 1 along with other diagrams such as FIGS. 2 and 3.

Figure 10:
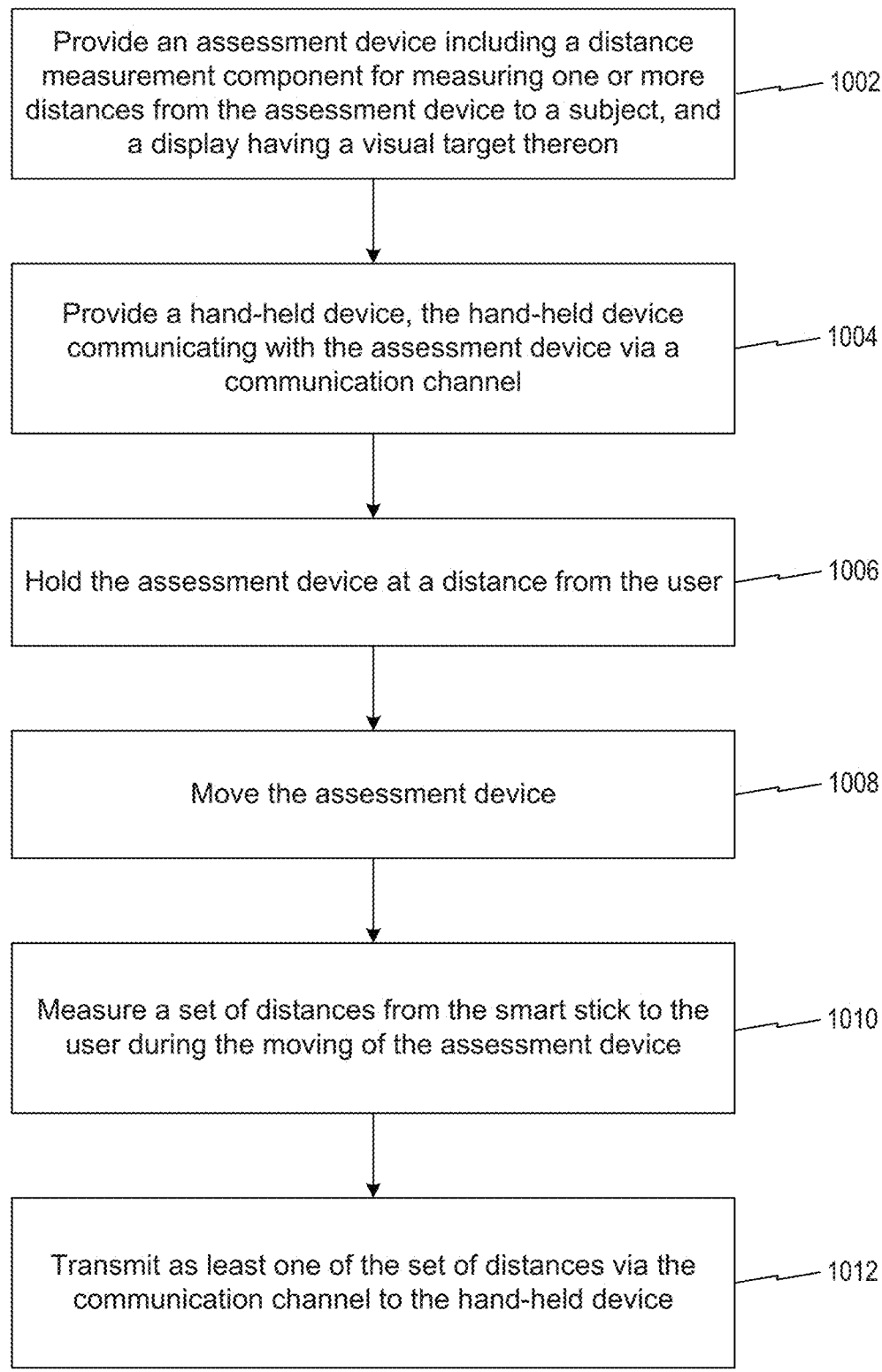
FIG. 10 is a flowchart illustrating an exemplary method for conducting general ocular function tests that may use the exemplary system in FIG. 1, according to an exemplary embodiment.

FIG. 10 is a flowchart illustrating an exemplary method for conducting general ocular function tests that may use the exemplary system in FIG. 1, according to an exemplary embodiment. The method may include: providing an assessment device, the assessment device including a portable carrier that includes a distance measurement component for measuring one or more distances from the assessment device to a subject, and a display having a visual target thereon (step 1002); providing a companion device, the companion device communicating with the assessment device via a communications channel (step 1004); holding the assessment device at a distance from the subject (step 1006); moving the assessment device (step 1008); recording a set of distances from the assessment device to the subject during the moving of the assessment device (1010); and transmitting the set of distances via the communications channel to the companion device, the set of distances being stored in the companion device (step 1012).

In step 1002, a subject or another user, such as a clinician, is provided an assessment device. The assessment device is capable of measuring and recording automatically a series of distance data that are measured from a portion of the subject to the assessment device (e.g., a displayed target on the assessment device).

In step 1004, a companion device is provided. The device may be any computing device that communicates with the assessment device, including a tablet, a smart cell phone, and a laptop on which an application program may be running for analyzing, displaying, and storing the distance data and/or other data and information.

In step 1006, the assessment device is held and positioned at a distance from the subject. Depending on specific ocular function test, the assessment device may be held by the subject or the clinician, and the distance from the subject may also vary.

In step 1008, the assessment device is being moved. The assessment device may be moved toward the subject, from left to right in a horizontal direction, or from up to down in a vertical direction, according to different ocular function tests.

In step 1010, a set of distance data from the assessment device to the subject is recorded during the moving of the assessment device. The set of distance data may be in an increasing or decreasing order depending on the specific ocular function test. For example, for NPC or NPA tests, the set of distance data is in a decreasing order as the assessment device moves towards the subject; for smooth pursuits tests, the set of distance data may be in a decreasing order as the assessment device moves from left to right in a horizontal direction Step 1012 may include transmitting the set of distances via the communications channel to the companion device. Additionally, other data or information may also be transmitted to the device for analysis, display and/or storage, such as error messages.

Although another user of the systems, devices and methods of the illustrative embodiments of the disclosure is described herein as a clinician, this is for purposes of example only. It is to be understood that another user can be anyone performing or assisting in the ocular assessment, which can include, without limitation, physicians, healthcare professionals, emergency medical technicians, sports medicine staff, military medics, teachers, coaches, and others. It is contemplated that the ease of use of the disclosed embodiments will make the collection of ocular assessment data performable by even untrained persons.

In the preceding specification, various exemplary embodiments and features have been described with reference to the accompanying drawings. It will, however, be evident that various modifications and changes may be made thereto, and additional embodiments and features may be implemented, without departing from the broader scope of the invention as set forth in the claims that follow. For example, advantageous results still could be if components in the disclosed systems were combined in a different manner and/or replaced or supplemented by other components. Other implementations are also within the scope of the following exemplary claims. The specification and drawings are accordingly to be regarded in an illustrative rather than restrictive sense. Moreover, it is intended that the disclosed embodiments and examples be considered as exemplary only, with a true scope of the present disclosure being indicated by the following claims and their equivalents.

What is claimed is:

1. A method for performing an ocular assessment on a subject with a portable assessment device, the assessment device comprising a visual display configured to display a visual target, a distance measurement component configured to measure distance between the subject and the assessment device, and a trigger configured to receive a user input, wherein the method comprises:
    measuring a first distance between the subject and the assessment device with the distance measurement component while the visual display is viewable by the subject;
    acquiring a plurality of distance measurements with the distance measurement component while the distance between the subject and the assessment device is decreased from the first distance, wherein the visual display displays the visual target during the acquisition of the plurality of distance measurements;
    upon receiving a user input signal from the trigger, measuring a final distance between the subject and the assessment device with the distance measurement component, wherein reception of the user input signal is associated with the occurrence of a predetermined ocular assessment event;
    evaluating the plurality of distance measurements to determine whether the final distance value is an outlier;
    if it is determined that the final distance value is not an outlier, performing at least one ocular function test based on the final distance value; and
    outputting results of the at least one ocular function test.

2. The method of claim 1, wherein the at least one ocular function test includes at least one of:
    a near point of convergence test, a near point of accommodation test, an eye tracking capability test, a smooth pursuit test, a saccades test, or a character-naming test.

3. The method of claim 1, wherein performing the at least one ocular function test comprises:
    performing a first ocular function test based on data derived from one eye of the subject; and
    performing a second ocular function test based on data derived from the other eye of the subject.

4. The method of claim 3, further comprising:
    outputting results of the first ocular function test and the second ocular function test, wherein the results indicate an ocular function status for each eye of the subject.

5. The method of claim 1, wherein the distance measurement component comprises:
    a camera having an image processing capability.

6. The method of claim 1, further comprising:
    determining whether the assessment device is optimally positioned using data of the distance measurement component; and
    generating a corrective visual target for display on the visual display if it is determined that the assessment device is not optimally positioned.

7. The method of claim 6, wherein the corrective visual target is configured to indicate to a user a corrective movement for positioning the assessment device at an optimal position thereof.

8. The method of claim 6, wherein the generation of the corrective visual target occurs while the distance between the subject and the assessment device is decreased from the first distance.

9. The method of claim 1, wherein the distance measurement component is configured to automatically measure distance between the assessment device and at least one of:
    the tip of the nose of the subject; or
    the forehead of the subject.

10. The method of claim 1, wherein the subject holds the assessment device and views the visual display during the measurement of the first distance, the acquisition of the plurality of distance measurements, and the measurement of the final distance.

11. The method of claim 10, wherein the visual display and the trigger are both situated on a first side of the assessment device.

12. The method of claim 1, wherein during the measurement of the first distance, the acquisition of the plurality of distance measurements, and the measurement of the final distance, a user other than the subject holds the assessment device and the subject views the visual display.

13. The method of claim 12, wherein the visual display is situated on a first side of the assessment device and the trigger is situated on a second side of the assessment device that is opposite from the first side.

14. The method of claim 1, wherein the predetermined ocular assessment event is at least one of:
    a time when a singular vision of the visual target is no longer maintained by the subject; or
    when at least one eye of the subject deviates outward.

15. The method of claim 1, wherein determining whether the final distance value is an outlier comprises:
    comparing the plurality of distance measurements against a target movement pattern of the assessment device; and
    if at least one of the distance measurements deviates from the target movement pattern by more than a predetermined acceptable distance, determining that the final distance value is an outlier.

16. The method of claim 1, further comprising generating a corrected final distance value if it is determined that the final distance value is an outlier, wherein generating the corrected final distance value comprises:
    comparing the plurality of distance measurements against a target movement pattern of the assessment device;
    identifying distance measurement values that deviate from the target movement pattern by less than a predetermined acceptable distance; and
    generating the corrected final distance value from the identified distance measurement values by extrapolation or a predictive algorithm.

* * * * *